United States Patent [19]

Kummer et al.

[11] 4,171,451

[45] Oct. 16, 1979

[54] MANUFACTURE OF BUTANEDICARBOXYLIC ACID ESTERS

[75] Inventors: Rudolf Kummer, Frankenthal; Heinz-Walter Schneider, Ludwigshafen; Rolf Platz, Mannheim; Peter Magnussen, Bad Durkheim; Franz-Josef Weiss, Weinheim, all of Fed. Rep. of Germany

[73] Assignee: BASF Aktiengesellschaft, Fed. Rep. of Germany

[21] Appl. No.: 883,216

[22] Filed: Mar. 3, 1978

[30] Foreign Application Priority Data

Mar. 25, 1977 [DE] Fed. Rep. of Germany ....... 2713195

[51] Int. Cl.$^2$ .............................................. C07C 67/38
[52] U.S. Cl. ............................. 560/204; 560/206
[58] Field of Search ................................ 560/204, 206

[56] References Cited

U.S. PATENT DOCUMENTS

| | | | |
|---|---|---|---|
| 2,542,767 | 2/1951 | Gresham et al. .................. | 560/204 |
| 3,507,891 | 4/1970 | Hearne et al. .................... | 560/233 |
| 3,778,466 | 12/1973 | Matsuda ............................ | 560/206 |
| 3,856,832 | 12/1974 | Ethyl Corporation ............ | 560/204 |
| 4,041,057 | 8/1977 | Fanning ............................ | 560/204 |

OTHER PUBLICATIONS

Matsuda, Bull. Chem. Soc. Japan, 46, pp. 524-530 (1973).

*Primary Examiner*—Jane S. Myers
*Attorney, Agent, or Firm*—Keil & Witherspoon

[57] ABSTRACT

A process for the manufacture of butanedicarboxylic acid esters, wherein (a) an aqueous cobalt salt solution is treated, at from 50° to 200° C. and under a pressure of from 50 to 500 bars, with excess carbon monoxide and hydrogen in the presence of active charcoal laden with cobalt carbonyl, (b) the resulting aqueous solution of cobalt carbonyl hydride is extracted with butadiene or with a hydrocarbon mixture containing butadiene and the aqueous phase is separated off, (c) the butadiene, or butadiene-hydrocarbon mixture, containing cobalt carbonyl hydride, cobalt carbonyl and butenyl-cobalt tricarbonyl is reacted with carbon monoxide and an excess of an alkanol of 1 to 4 carbon atoms in the presence of from 0.5 to 2 moles, per mole of butadiene, of a tertiary nitrogen base having a $pK_a$ of from 3 to 11, at from 80° to 150° C. under a pressure of from 300 to 2,000 bars, and (d) the resulting reaction mixture is freed from the tertiary nitrogen base contained therein, except for from 0.1 to 0.3 mole per mole of pentenoic acid ester, and from excess hydrocarbons, the pentenoic acid ester remaining in the reaction mixture is reacted with carbon monoxide and an excess of an alkanol of 1 to 4 carbon atoms at from 140° to 200° C. and under pressures of from 100 to 400 bars in the presence of the amounts of cobalt carbonyl and tertiary nitrogen base contained in the reaction mixture, and excess alkanol and free nitrogen base are then distilled off, and (e) the reaction mixture which remains, and which contains cobalt catalyst, the butanedicarboxylic acid ester and by-products is treated with an oxidizing agent in an aqueous acid medium and the mixture is separated into an organic phase, from which the butanedicarboxylic acid ester is isolated by distillation, and into an aqueous phase containing cobalt salts.

Butanedicarboxylic acid esters may be used for the manufacture of adipic acid and of nylons.

5 Claims, No Drawings

MANUFACTURE OF BUTANEDICARBOXYLIC ACID ESTERS

The present invention relates to a process for the manufacture of a butanedicarboxylic acid ester, by reacting butadiene or a hydrocarbon mixture containing butadiene with carbon monoxide and a lower alkanol in the presence of a tertiary nitrogen base and cobalt carbonyl at from 80° to 150° C. under superatmospheric pressure and further reacting the resulting pentenoic acid ester with carbon monoxide and a lower alkanol at from 140° to 200° C., under superatmospheric pressure, to give the butanedicarboxylic acid ester.

Bull. Chem. Soc. Japan 46 (1973), 524 et seq. discloses a twostage process for the manufacture of adipic acid esters from butadiene, wherein butadiene is first reacted with carbon monoxide and an alkanol in the presence of cobalt carbonyl and a nitrogen base, e.g. pyridine or isoquinoline, and in a subsequent stage the resulting pentenoic acid ester is reacted further, without removing the catalyst, with carbon monoxide and an alkanol to give the adipic acid ester. However, when carrying out this process industrially it is necessary to recover and recycle the catalyst. Thus, in the process disclosed in U.S. Pat. No. 3,778,466, the residue containing the catalyst, obtained after distilling off the desired products, is re-used for the carbonylation. However, it has been found that after having been used, for example, 4 times, the activity of the catalyst declines substantially. This is attributable to the fact that on the one hand the distillation damages the catalyst, since cobalt carbonyl complexes are not heat-stable, whilst on the other hand the carbonylation produces by-products which influence the carbonylation and must therefore be removed continuously. Attempts have also already been made to separate the desired products from the catalyst-containing residue, after the carbonylation, by an extraction. For example, German Laid-Open Application DOS No. 2,159,139 discloses a process in which the methanol-containing carbonylation mixture is extracted with hydrocarbons. It is true that this makes it possible to isolate the desired products without damaging the catalyst and to recycle the catalyst-containing methanolic solution to the carbonylation reaction. However, this extractive separation is unsuitable for removing by-products, e.g. butadiene polymers, which are formed during carbonylation. Accordingly, these by-products progressively accumulate if the catalyst solution is repeatedly re-used, and interfere with the carbonylation.

It is an object of the present invention to modify the carbonylation of butadiene to give butanedicarboxylic acid esters, in such a way that the catalyst metal is substantially recovered in a form in which it can be re-used for the carbonylation, and at the same time the harmful by-products are removed.

We have found that this object is achieved in a process for the manufacture of a butanedicarboxylic acid ester, by reacting butadiene or a hydrocarbon mixture containing butadiene with carbon monoxide and an excess of an alkanol of 1 to 4 carbon atoms in the presence of a tertiary nitrogen base and a cobalt carbonyl compound at from 80° to 150° under superatmospheric pressure and then reacting the resulting pentenoic acid ester further, without removing the cobalt catalyst, with carbon monoxide and an alkanol of 1 to 4 carbon atoms at from 140° to 200° C. under superatmospheric pressure to give the butanedicarboxylic acid ester, wherein (a) an aqueous cobalt salt solution is treated, at from 50° to 200° C. and under a pressure of from 50 to 500 bars, with excess carbon monoxide and hydrogen in the presence of active charcoal laden with cobalt carbonyl, (b) the resulting aqueous solution of cobalt carbonyl hydride is extracted with butadiene or with a hydrocarbon mixture containing butadiene and the aqueous phase is separated off, (c) the butadiene, or butadiene-hydrocarbon mixture, containing cobalt carbonyl hydride, cobalt carbonyl and butenyl-cobalt tricarbonyl, is reacted with carbon monoxide and an excess of an alkanol of 1 to 4 carbon atoms in the presence of from 0.5 to 2 moles, per mole of butadiene, of a tertiary nitrogen base having a $pK_a$ of from 3 to 11, at from 80° to 150° C. under a pressure of from 300 to 2,000 bars, (d) the resulting reaction mixture is freed from the tertiary nitrogen based contained therein, except for from 0.1 to 0.3 mole per mole of pentenoic acid ester formed, and from excess hydrocarbons, the pentenoic acid ester remaining in the reaction mixture is reacted with carbon monoxide and an excess of an alkanol of 1 to 4 carbon atoms at from 140° to 200° C. and under a pressure of from 100 to 400 bars in the presence of the amounts of cobalt carbonyl and tertiary nitrogen base contained in the reaction mixture, and excess alkanol and free nitrogen base are then distilled off, and e) the reaction mixture which remains, and which contains cobalt catalyst, the butanedicarboxylic acid ester and by-products, is treated with an oxidizing agent in an aqueous acid medium and the mixture is separated into an organic phase, from which the butanedicarboxylic acid ester is isolated by distillation, and into an aqueous phase containing cobalt salts.

The new process has the advantage that the by-products are removed and are not recycled to the carbonylation reaction, and at the same time the catalyst metal is recovered virtually quantitatively and when it is re-used the activity of the catalyst for the carbonylation stages is unimpaired. As a result, high yields can be achieved even after prolonged operation. Further, the new process permits continuous operation on an industrial scale, without adverse consequences.

In the first stage (stage a) an aqueous cobalt salt solution is reacted with carbon monoxide and hydrogen in excess at from 50° to 200° C. under a pressure of from 50 to 500 bars in the presence of active charcoal laden with cobalt carbonyl. The cobalt salts used are preferably water-soluble salts of fatty acids, especially formate, acetate, propionate and butyrates. Cobalt formate and cobalt acetate have proved particularly suitable. It is advantageous to start from solutions which contain from 0.5 to 5% by weight of cobalt, calculated as metal, especially from 1 to 3% by weight of cobalt, in the form of the above salts. In general, the above gas mixture contains carbon monoxide and hydrogen in a volume ratio of from 4:1 to 1:2, especially from 2:1 to 1:1. An approximately equimolar mixture of carbon monoxide and hydrogen has proved particularly suitable. Advantageously, the mixture of carbon monoxide and hydrogen is employed in excess, for example in up to 5 times the stoichiometric amount. It is advantageous to maintain the temperature at from 100° to 170° C. and the pressure at from 100 to 400 bars. Further, it has proved advantageous if the aqueous cobalt salt solution contains up to 20% by weight, especially from 3 to 10% by weight, of an inert neutral salt, preferably an alkali metal salt of a non-oxidizing acid, e.g. an alkali metal sulfate or an alkali metal phosphate.

The treatment in stage a is carried out in the presence of active charcoal. Examples of suitable types of active charcoal are peat charcoal, animal charcoal and sugar charcoal. The first-mentioned has proved particularly suitable. The active charcoal is advantageously laden with cobalt carbonyl until saturated. This is generally achieved by passing an aqueous solution of a cobalt salt, together with the above gas mixture of carbon monoxide and hydrogen, over the active charcoal, under the stated reaction conditions, until the charcoal is saturated, i.e. until cobalt carbonyl or cobalt carbonyl hydride is analytically detectable in the material leaving the active charcoal.

In general, the treatment is carried out in a treatment zone which advantageously has a length to diameter ratio of from 5:1 to 50:1 and in which the active charcoal is as a rule present as a fixed bed. Preferably, from 1.5 to 15 g of cobalt, calculated as metal, in the form of the above salts are introduced per hour per kilogram of active charcoal.

The aqueous solution thus obtained, containing cobalt carbonyl hydride, unconverted cobalt salts and liberated acid is fed to the second stage (stage b), preferably together with the unconsumed mixture of carbon monoxide and hydrogen, advantageously without letting-down. In stage b, cobalt carbonyl hydride is extracted with butadiene or butadiene-containing hydrocarbon mixtures, which will be discussed in more detail below. It is possible to carry out the extraction with the entire amount of butadiene required for the carbonylation or with only a part thereof. Advantageously, from 5 to 30 moles of butadiene are used per gram atom of cobalt to be extracted. The extraction is carried out in counter-current or cocurrent, in an apparatus industrially used for extraction, e.g. a column or static mixer. During the extraction, the temperature is preferably maintained at from 20° to 100° C. and the pressure at from 5 to 300 bars. The mixture is then separated into an aqueous phase and an organic phase. If, for example, the extraction is carried out in a pressure tube filled with Raschig rings, separation into an organic phase and an aqueous phase at the same time occurs in the upper part of the tube. The mixture of carbon monoxide and hydrogen, used as one of the components, is simultaneously removed as the gaseous phase. The cobalt content of the organic phase leaving stage b is in general from 1 to 5% by weight. It is assumed that the cobalt carbonyl is present in the organic phase as a waterinsoluble complex with butadiene.

In stage c, the organic phase is then reacted, in the presence of from 0.5 to 2 moles, per mole of butadiene, of a tertiary nitrogen base having a $pK_a$ of from 3 to 11, with the proviso that the said base should preferably be lower-boiling than the particular pentenoic acid ester to be produced, with an excess of an alkanol of 1 to 4 carbon atoms and carbon monoxide at from 80° to 150° C. and under a pressure of from 300 to 2,000 bars.

If the extraction were carried out with less than the total amount of butadiene, or butadiene-containing hydrocarbon mixture, required for the carbonylation, the requisite additional amount of starting materials is added to stage c. It should be noted that instead of pure butadiene, butadiene-containing hydrocarbon mixtures may be used advantageously. Such hydrocarbon mixtures contain, in addition to butadiene, saturated hydrocarbons of 3 to 5 carbon atoms and monoolefinically unsaturated olefins of 3 to 5 carbon atoms. The butadiene content should as a rule be more than 10% by weight. Industrially, $C_4$-cuts, in particular, are used as the starting mixture. Such a cut is defined as any mixture of predominantly unbranched hydrocarbons of 4 carbon atoms, which contains more than 10% by weight of 1,3-butadiene (butadiene) and more than 15% of butenes. Depending on the origin of the cut, the individual components are normally present in the following proportions in such mixtures:

butadiene—from 10 to 70, on average from 40 to 60, % by weight isobutene—from 15 to 40, on average from 20 to 35, % by weight but-1-ene—from 10 to 40, on average from 10 to 25, % by weight but-2-ene—from 5 to 20, on average from 5 to 15, % by weight butanes—from 1 to 10, on average from 1 to 10, % by weight butynes—from 0.1 to 3, on average from 0.1 to 3, % by weight Such $C_4$-cuts are obtained, for example, on dehydrogenating butane or butene, or as by-products of the production of ethylene by cracking of naphtha or of higher hydrocarbon cuts.

Preferred suitable tertiary nitrogen bases are N-heterocyclic compounds, e.g. pyridine ($pK_a$ 5.3), methylpyridines, e.g. 3-picoline ($pK_a$ 6.0), and isoquinoline ($pK_a$ 5.4) as well as trialkylamines, e.g. trimethylamine ($pK_a$ 9.8) or triethylamine ($pK_a$ 11.0). Pyridine is industrially of particular importance.

It has proved particularly advantageous to use from 0.6 to 1.5 moles of tertiary nitrogen base per mole of butadiene.

It is preferred to use a tertiary nitrogen base which is lower-boiling than the particular pentenoic acid ester to be produced.

Suitable alkanols of 1 to 4 carbon atoms are methanol, ethanol, propanol, butanol and isobutanol. The use of methanol is particularly preferred. It is preferred to use from 1.5 to 4 moles of alkanol per mole of butadiene.

The reaction is preferably carried out at from 120° to 140° C. under a pressure of from 600 to 1,200 bars. As a rule, from 0.01 to 0.1 gram atom of cobalt, in the form of the above cobalt carbonyl complexes, is used per mole of butadiene.

In this context it should be noted that when using mixtures of compounds of 4 carbon atoms, the butenes which are also present do not react, under the stated reaction conditions, to give the corresponding carboxylic acid esters, though such reaction would have been expected from German Laid-Open Application DOS. No. 2,023,690.

In addition to unconverted butadiene, the reaction mixture obtained may contain other hydrocarbons, tertiary nitrogen bases, cobalt carbonyl, unconverted alkanols, the pentenoic acid esters formed as the desired products, and by-products, e.g. valeric acid esters, vinylcyclohexene, butenyl ketones and butyl ketones, as well as butadiene polymers.

After letting down, the reaction mixture obtained is freed from the tertiary nitrogen bases contained therein, down to from 0.1 to 0.3 mole per mole of pentenoic acid ester, and is also freed from any excess hydrocarbons (stage d). This may be effected by distillation or other methods of separation, e.g. extraction. Advantageously, the tertiary nitrogen bases and any excess hydrocarbons are removed by distillation under reduced pressure. In doing so, the bottom temperature should not exceed 75°, in order to avoid decomposing the cobalt catalyst. Depending on the choice of the alkanol used, part or all of the excess alkanol may distil off at the same time.

The pentenoic acid ester remaining in the reaction mixture is reacted with carbon monoxide and an excess of an alkanol of 1 to 4 carbon atoms, if necessary after adding back the requisite amount of alkanol, at from 140° to 200° C. and under a pressure of from 100 to 400 bars, in the presence of the amount of cobalt catalyst and tertiary nitrogen base contained in the reaction mixture. Advantageously, the reaction is carried out at from 150° to 180° C. under a pressure of from 100 to 400 bars. Preferably, the amount of alkanol present is from 1.5 to 4 moles per mole of pentenoic acid ester. Further, it has proved advantageous to add a few percent by volume of hydrogen, e.g. from 1 to 4 percent by volume, to the carbon monoxide in order to increase the rate of reaction. After letting down, the excess alkanol and the free tertiary nitrogen base are distilled from the reaction mixture obtained. The chemically bound tertiary nitrogen base (from 1 to 2 moles per gram atom of cobalt) is not distilled off during this stage. To avoid undesirable decomposition of the cobalt complex, with formation of cobalt metal, it has proved advantageous to pass a slow stream of carbon monoxide or of a gas containing carbon monoxide into the bottom of the column.

The reaction mixture which remains, and which contains catalyst, butanedicarboxylic acid ester and by-products, is treated, in stage e, with an oxidizing agent in an aqueous acid medium. Particularly suitable oxidizing agents are those which do not contaminate the reaction mixture, e.g. hydrogen peroxide, oxygen or an oxygen-containing gas. The use of a gas containing molecular oxygen, especially the use of air, is particularly preferred. The oxidizing agent is used in an amount of at least two oxidation equivalents per mole of cobalt compound. Preferably, however, an excess is used. In practice it has proved advantageous to use from 30 to 300 liters (S.T.P.) of air per kg of reaction mixture.

In general, the amount by weight of water used if from 0.1 to 10 times of the reaction mixture, advantageously from 0.2 times to an equal amount. The pH is advantageously from 3 to 6. Suitable acids are non-oxidizing mineral acids and fatty acids. The aqueous acid solution obtained in stage b after removing the butadiene containing cobalt carbonyl hydride is particularly suitable for use as the acid. For example, when starting from cobalt acetate, such a solution contains unconverted cobalt acetate and acetic acid. If necessary, a suitable fatty acid may additionally be introduced. It is necessary to ensure under all circumstances that sufficient acid is present to keep the cobalt salt in solution. The same is true of the amount of water to be used. In order that the cobalt solution shall not be too dilute, it is advantageous to recycle the aqueous cobalt-containing solution to the treatment chamber and only remove a small bleed stream, corresponding to the amount introduced.

The treatment is advantageously carried out at from 80° to 160° C. Temperatures of from 100° to 130° C. have proved particularly suitable. Depending on the degree of mixing, the reaction may be complete after merely a few seconds, and in many cases even within a fraction of a second. To ensure good mixing it is advantageously to feed the reaction mixture into the aqueous acid solution together with the oxidizing agent, for example air, in a finely dispersed form.

After the treatment, the liquid phase is separated, for example by decanting, into an organic phase and an aqueous phase. We have found that the phase separation is advantageously facilitated if the aqueous acid medium contains inert neutral salts, for example alkali metal salts of non-oxidizing agents, e.g. sodium sulfate, in amounts of up to 20%. Furthermore, it is advantageous to add up to 20% by weight of hydrocarbons to the organic phase. The excess hydrocarbons distilled off in stage d after the first carbonylation are particularly suitable for this purpose.

Fractional distillation of the organic phase gives residual tertiary nitrogen base and unconverted pentenoic acid ester, which are recycled to the carbonylation, and a mixture of butanedicarboxylic acid esters (from 80 to 85% by weight of adipic acid ester, from 11 to 15% by weight of 2-methylglutaric acid ester and from 3 to 6% by weight of 2-ethylsuccinic acid ester). The ester mixture can be used for the manufacture of diols or of polyesters. The adipic acid ester obtainable from the ester mixture by fractional distillation may be used for the manufacture of adipic acid, of nylon (adipic acid/hexamethylenediamine) salt, adipodinitrile and hexane-1,6-diol.

The aqueous phase which contains cobalt salts and may contain some free acid is advantageously recycled to stage a to serve as the starting solution for the manufacture of cobalt carbonyl hydride. The process according to the invention is outstandingly suitable for continuous industrial operation.

The Example which follows illustrates the process of the invention.

EXAMPLE

A high pressure tube which is filled with 600 ml of active charcoal (from Norit, particle size from 3 to 5 mm) is charged with 180 ml per hour of an aqueous cobalt acetate solution which contains 2.5% by weight of cobalt$^{2+}$ and 10% by weight of sodium sulfate. In addition, 50 liters (S.T.P.) per hour of an equimolar mixture of carbon monoxide and hydrogen are introduced. A temperature of 120° C. and a pressure of 300 bars is maintained. The solution taken off the other part of the tube contains 0.65% by weight of cobalt$^{2+}$ and 1.85% by weight of cobalt in the form of cobalt carbonyl hydride, as well as the corresponding amount of acetic acid. After letting down to 20 bars, this solution is thoroughly mixed, at room temperature, with 310 ml of a $C_4$-cut which contains 43% by weight of butadiene (1.57 moles). After separating the phases, the $C_4$-cut contains 3.7 g of cobalt in the form of cobalt carbonyl compounds. This cobalt-containing $C_4$-cut is then fed to a high pressure vessel of 1.9 liters capacity, and in addition 127 ml (1.57 moles) of pyridine, 127 ml (3.14 moles) of methanol and 60 liters (S.T.P.) of carbon monoxide per hour are introduced. The carbonylation takes place at 130° C. and 600 bars. The product taken off at the top of the high pressure vessel is let down, resulting in excess hydrocarbons of 4 carbon atoms being removed in the gaseous form, together with excess carbon monoxide. These hydrocarbons contains virtually no butadiene. Accordingly, the conversion is quantitative. Per hour, about 52 g of methanol and 100 g of pyridine are distilled from the material leaving the reactor, the distillation being carried out under reduced pressure so as not to affect the catalyst. The maximum bottom temperature during distillation is 65° C. The bottom material, which contains 3.7 g of cobalt as a carbonyl complex and 165 g (1.44 moles) of pentenoic acid ester is fed continuously, together with 117 ml (2.88 moles) of methanol and 55 liters (S.T.P.) of carbon monoxide, containing 2% by volume of hydrogen, into the bottom of a further high pressure vessel having a capacity of 1.7 liters. The carbonylation is carried out at 170° C. under a pressure of 150 bars. Analysis by gas chromatography of the material leaving the reactor (at an hourly rate of 328 g) shows that of the pentenoic acid ester introduced, 4 mole % have been converted to valeric acid ester, 4 mole % to dimethyl ethylsuccinate, 11 mole % to dimethyl methylglutarate, 73 mole % to dimethyl adipate and 1 mole % to acetals of 4- and 5-formylvaleric acid ester. 7 mole % of the pentenoic acid ester have not undergone reaction but have been partially isomerized to methyl pent-2-enoate. The selectivity of the conversion to butanedicarboxylic acid esters is accordingly 87%, and the selectivity of conversion to dimethyl adipate is 72%, based on butadiene employed. The excess methanol and the free pyridine are distilled from the product in a further column whilst passing in about 50 liters (S.T.P.) of carbon monoxide per hour. The bottom residue (265 g/hour) is thoroughly mixed with 200 ml per hour of the aqueous solution which is obtained in the extraction stage and contains acetic acid and sodium sulfate, the mixing being carried out in a tube filled with Raschig rings, at 100° C., whilst passing about 50 liters (S.T.P.) of air per hour through the tube. After separation, 200 ml of aqueous cobalt acetate solution containing 2.45% by weight of cobalt$^{2+}$ are obtained and after distilling off small amounts of pyridine this solution is fed to stage a, where cobalt carbonyl is formed. The organic phase is separated by fractional distillation into pyridine (about 5 g), valeric acid ester (6.5 g), pentenoic acid ester (11.5 g) and dimethyl butanedicarboxylate (220 g). The last-mentioned contains 181 g of dimethyl adipate.

We claim:
1. In a process for the manufacture of a butanedicarboxylic acid ester, by reacting butadiene or a hydrocarbon mixture containing butadiene with carbon monoxide and an alkanol of 1 to 4 carbon atoms in the presence of a tertiary nitrogen base and a cobalt carbonyl at from 80° to 150° C. under superatmospheric pressure and then reacting the resulting pentenoic acid ester, without removing the catalyst, with carbon monoxide and an alkanol of 1 to 4 carbon atoms at from 140° to 200° C. under superatmospheric pressure to give the butanedicarboxylic acid ester, the improvement wherein
(a) an aqueous cobalt salt solution is treated, at from 50° to 200° C. and under a pressure of from 50 to 500 bars, with excess carbon monoxide and hydrogen in the presence of active charcoal laden with cobalt carbonyl,
(b) the resulting aqueous solution of cobalt carbonyl hydride is extracted with butadiene or with a hydrocarbon mixture containing butadiene and the aqueous phase is separated off,
(c) the butadiene, or butadiene-hydrocarbon mixture, containing cobalt carbonyl hydride, cobalt carbonyl and butenyl-cobalt tricarbonyl is reacted with carbon monoxide and an excess of an alkanol of 1 to 4 carbon atoms in the presence of from 0.5 to 2 moles, per mole of butadiene, of a tertiary nitrogen base having a pK$_a$ of from 3 to 11, at from 80° to 150° C. under a pressure of from 300 to 2,000 bars,
(d) the resulting reaction mixture is freed from the tertiary nitrogen base contained therein, except for from 0.1 to 0.3 mole per mole of pentenoic acid ester, and from excess hydrocarbons, the pentenoic acid ester remaining in the reaction mixture is reacted with carbon monoxide and an excess of an alkanol of 1 to 4 carbon atoms at from 140° to 200° C. and under pressures of from 100 to 400 bars in the presence of the amounts of cobalt carbonyl and tertiary nitrogen base contained in the reaction mixture, and excess alkanol and free nitrogen base are then distilled off, and
(e) the reaction mixture which remains, and which contains cobalt catalyst, the butanedicarboxylic acid ester and by-products is treated with an oxidizing agent in an aqueous acid medium and the mixture is separated into an organic phase, from which the butanedicarboxylic acid ester is isolated by distillation, and into an aqueous phase containing cobalt salts.

2. The process of claim 1, wherein an aqueous solution which contains from 0.5 to 4% by weight of cobalt in the form of water-soluble cobalt salts of fatty acids and up to 20% by weight of inert neutral salts is used.

3. The process of claim 1, wherein the aqueous phase separated off in stage b is used as the aqueous acid medium in stage e and the aqueous phase containing cobalt salts, obtained in stage e, is used in stage a for the manufacture of cobalt carbonyl hydride.

4. The process of claim 1, wherein pyridine is used as the tertiary nitrogen base.

5. The process of claim 1, wherein methanol is used as the alkanol.

* * * * *